United States Patent [19]
Carusillo et al.

[11] Patent Number: 5,136,469
[45] Date of Patent: Aug. 4, 1992

[54] POWERED SURGICAL HANDPIECE INCORPORATING SEALED MULTI SEMICONDUCTOR MOTOR CONTROL PACKAGE

[75] Inventors: Steven J. Carusillo, Kalamazoo; Ralph S. Robertson, Delton; John Izenbaard, Vicksburg, all of Mich.

[73] Assignee: Stryker Corporation, Kalamazoo, Mich.

[21] Appl. No.: 731,413

[22] Filed: Jul. 17, 1991

[51] Int. Cl.⁵ .............................. H05K 1/18
[52] U.S. Cl. .................... 361/397; 388/937
[58] Field of Search ............ 361/380, 381, 386, 388, 361/395, 397, 399, 401; 174/50.54, 51, 52.1, 52.3, 52.4; 206/328; 357/74, 80, 81, 82; 388/937

[56] References Cited
U.S. PATENT DOCUMENTS

| | | | |
|---|---|---|---|
| 4,758,927 | 7/1988 | Berg | 361/401 |
| 4,847,731 | 7/1989 | Smolley | 361/385 |
| 4,923,404 | 5/1990 | Redmond et al. | 439/71 |
| 4,999,740 | 3/1991 | Ilardi et al. | 361/386 |
| 5,003,429 | 3/1991 | Baker et al. | 361/386 |

OTHER PUBLICATIONS
Data sheets published by Siliconix Incorporated, pp. 4-343 and 8-1.

Primary Examiner—Bentsu Ro
Attorney, Agent, or Firm—Flynn, Thiel, Boutell & Tanis

[57] ABSTRACT

A compact, hermetically sealed, heat dissipating electric power unit comprises a P.C. board having a hole therethrough. A semiconductor electric power control device fits loosely in the hole. A backer of heat and electric current conductive material is bonded in heat and electric current conductive contact (1) with the P.C. board around the perimeter of the hole to hermetically seal the corresponding end of the hole and (2) with an opposed first electrode of the device, the backer acting as an electric current path and at least part of a heat sink for the device, the backer and P.C. board having similar thermal expansion coefficients so as to maintain the hermetic seal. An electrically conductive ground ring is electrically conductively fixed on the other face of the P.C. board and is electrically connected to the second electrode of the device and acts as a further electric current path. A cover of ceramic material has a thermal expansion coefficient similar to that of the core. The cover loosely overlies the device and has a perimeter portion sealed to the P.C. board to form therewith and with the backer a hermetically sealed chamber containing the device.

9 Claims, 2 Drawing Sheets

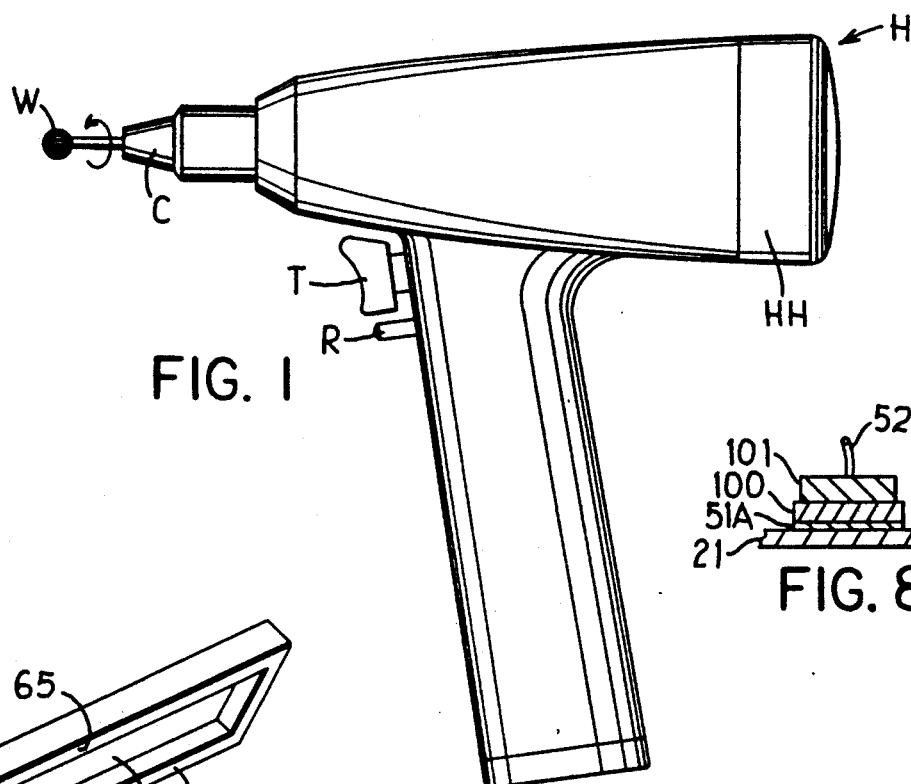
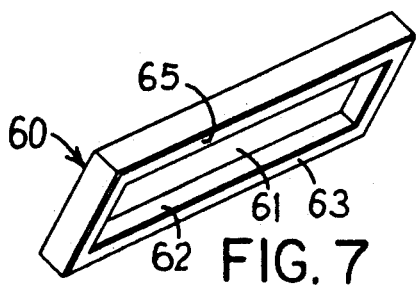
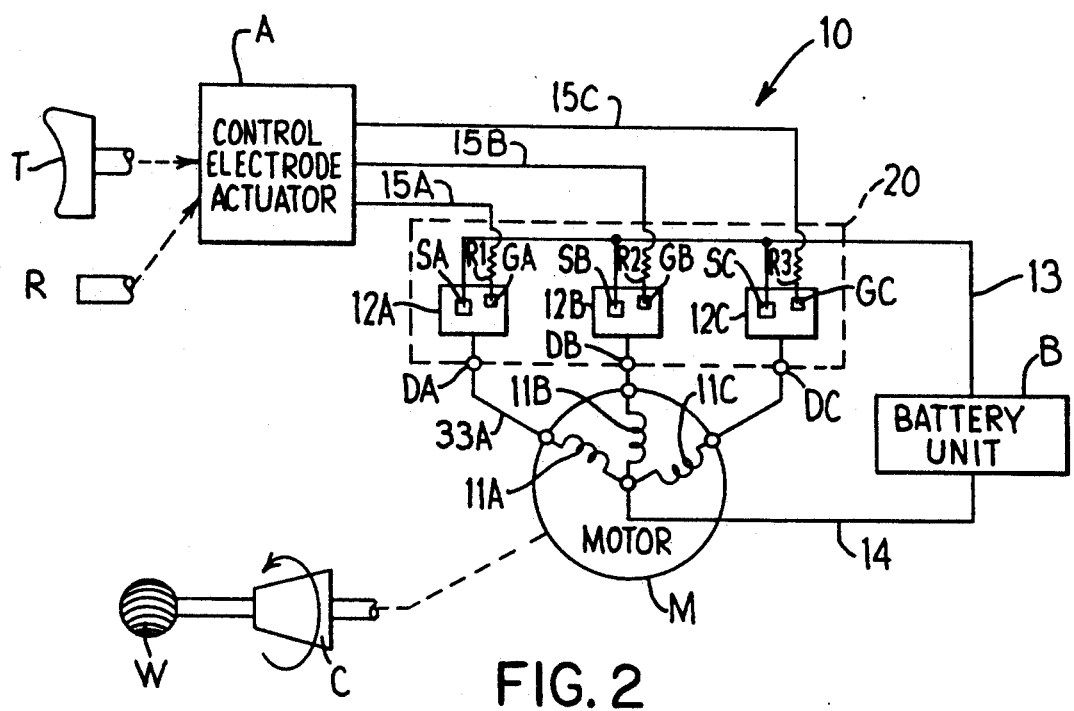

5,136,469

POWERED SURGICAL HANDPIECE INCORPORATING SEALED MULTI SEMICONDUCTOR MOTOR CONTROL PACKAGE

FIELD OF THE INVENTION

This invention relates to a powered surgical handpiece and particularly to such a handpiece incorporating a sealed multi semiconductor motor control package.

BACKGROUND OF THE INVENTION

It is known to mount semiconductor electric power control devices, such as FET's, on temperature resistant P.C. boards, for example of temperature resistant ceramic material, wherein the main current carrying electrodes of the semiconductor device are electrically connected, as by soldering, to conventional conductive foils bonded onto the ceramic core of the P.C. board and wherein the semiconductor devices are mounted directly on the P.C. board.

An example of such a structure is a four channel transistor pack (MOD. 200A) manufactured by Siliconix Inc., Santa Clara, Calif.

However, the present Applicant has observed that relatively high electric power and current is handled by the semiconductor devices which energize the tool driving motor of a surgical handpiece, and that as a result, such semiconductor power control devices may get excessively hot, thereby reducing the reliability and operating life thereof.

Further, the present Applicant has observed that the electric power control units of powered surgical handpieces operate in an adverse environment in which liquids and vapors (for example patient body liquids and irrigation liquids present at the operating site) or steam from the sterilization process may, if allowed to come in contact with the power control devices and electric connections thereto, interfere with proper operation of the surgical tool.

Applicant has further observed that it would be desirable to both dissipate (e.g. sink) the excessive heat generated by the power control devices during motor operation and hermetically seal the power control devices and their electrode connections while maintaining the power control package as compact as possible so as to fit within a relatively compact surgical handpiece housing. However, the need for compactness, hermetic sealing and heat dissipation are in conflict with each other and, as far as the present Applicant is aware, no satisfactory solution has been available up to this time. The present invention has resulted from an attempt to meet these conflicting requirements.

Accordingly, the objects and purposes of the present invention include provision of a powered surgical handpiece and an electric power control package therefore in which the electric power control devices for energizing the handpiece motor are compactly housed, provided with effective heat sinking to limit the operating temperature thereof and are enclosed in a hermetically sealed housing to prevent intrusive liquid or vapor contact therewith.

Further objects and purposes of the invention will be apparent to persons acquainted with apparatus of this general type upon reading the following specification and inspecting the accompanying drawings.

SUMMARY OF THE INVENTION

A compact, hermetically sealed, heat dissipating electric power unit comprises a P.C. board having a hole therethrough. A semiconductor electric power control device fits loosely in the hole. A backer of heat and electric current conductive material is bonded in heat and electric current conductive contact (1) with the P.C. board around the perimeter of the hole to hermetically seal the corresponding end of the hole and (2) with an opposed first electrode of the device, the backer acting as an electric current path and at least part of a heat sink for the device, the backer and P.C. board having similar thermal expansion coefficients so as to prevent breakage of the substrate due to thermal cycling. An electrically conductive ground ring is electrically conductively fixed on the other face of the P.C. board to form a hermetic seal and is electrically connected to the second electrode of the device and acts as a further electric high current path. A cover of ceramic material has a thermal expansion coefficient similar to that of the core. The cover loosely overlies the device and has a perimeter portion sealed to the upper surface of the ground ring to form therewith and with the backer a hermetically sealed chamber containing the device.

BRIEF DESCRIPTION OF THE DRAWINGS

FIG. 1 is a side elevational view of an electric motor powered, surgical handpiece embodying the invention.

FIG. 2 is a diagram schematically illustrating a trigger actuated, electric power system of the hand-piece of FIG. 1.

FIG. 7 is a pictorial view, viewed from the bottom and one end inside of the cover.

FIG. 8 is an enlarged fragmentary sectional view substantially taken on the line 8—8 of FIG. 3.

DETAILED DESCRIPTION

Figure 3:
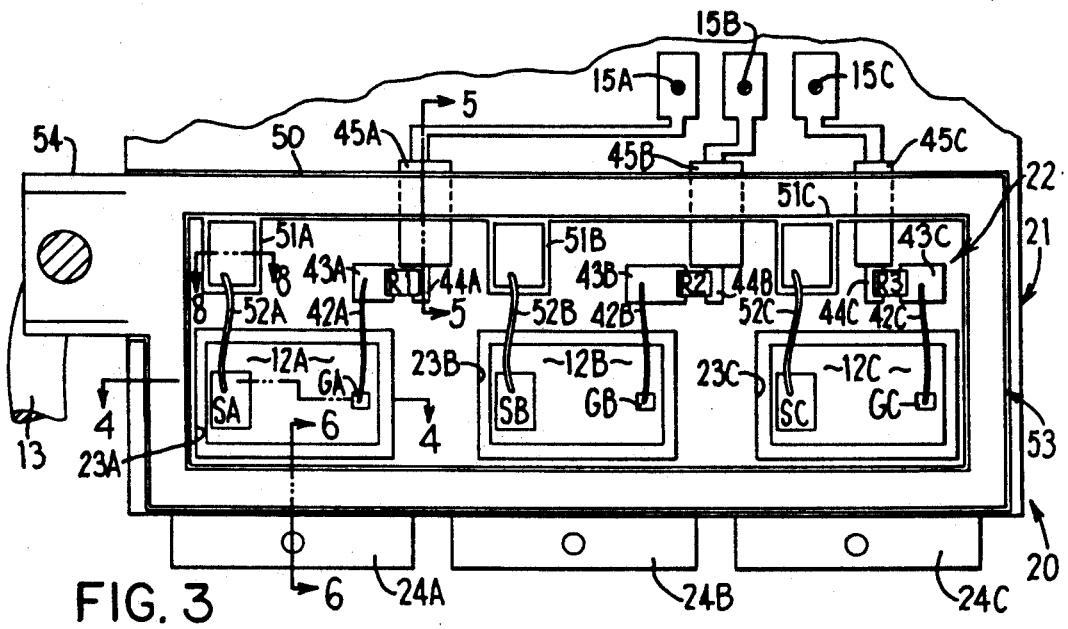
FIG. 3 is a plan view of a motor control package of the kind schematically illustrated in FIG. 2, with the cover removed.

FIG. 1 discloses a powered surgical handpiece H having a chuck C having a trigger T manually actuable to control movement of the chuck C and a working member (tool) W fixed in the chuck C. A wide variety of surgical handpieces H are known, capable of driving working members W of various types with a variety of motions. Examples include rotatably driven drills and reamers, oscillating saws, reciprocating saws, etc. In handpieces of this type it is known to drive the working member at alternative speeds and/or in forward or reverse directions. Handpieces of this general kind, including electrically driven ones, have been manufactured by the Assignee of the present invention for many years.

FIG. 2 schematically discloses an example of an electric power system 10 through which appropriate actuation of the trigger T results in the desired movement of the working member W, which electric power system 10 may be enclosed in the housing HH of the FIG. 1 handpiece H. In the example shown, the motor M is of a kind including at least one (here three) windings, or coils, energizable from a battery B to move (here rotate) the chuck C and thereby correspondingly move the working member W. Current from the battery B is applied to the motor coils 11A, 11B and 11C by conventional semiconductor power switch devices 12A, 12B and 12C, such as power transistors, field effect transistors, etc., connected in current loop with the respective coils and the battery B for thereby energizing the motor M. In the FIG. 2 example, field effect transistors (FET's) 12A, 12B and 12C are schematically shown.

In the example shown, the FET's 12A–C have respective source electrodes SA, SB and SC connected in common at 13 to one pole of the battery B, the opposite pole of which is connected at 14 to the common ends of the motor coils 11A–C respectively. The free ends of the motor coils 11A–connect respectively to the drains DA, DB and DC of the respective field effect transistors 12A, 12B and 12C. The field effect transistors 12A, 12B and 12C have respective control electrodes (gates) GA, GB and GC actuable through respective resistors R1, R2 and R3 by respective output lines 15A, 15B and 15C of a conventional control electrode actuator circuit A in turn conventionally controlled by the trigger T. It will be understood that the motor M may be of a variety of types including types having a single or multiple (as here) coil arrangement, that the electric power handling semiconductor devices 12A–12C may be provided singly or in multiple (as here) and that the character of the output on the output line or lines 15 of the control electrode actuator A may be of any suitable kind capable of driving the control electrodes of the devices 12 and motor M. In the particular embodiment shown, rotation of the chuck C by the motor M is obtained by proper sequential actuation of the motor coils 11A–C in a conventional manner and the actuator A provides gate signals in the correspondingly proper sequence and in a conventional manner on the gate control lines 15A–C, such sequence controlling forward or reverse actuation of the motor M in a conventional manner, as in response to actuation of a reverse switch R. Motor speed M can be controlled in the FIG. 2 example, for example by pulsing the electrical output of the actuator A on the lines 15A–C to the gates GA–C and varying the length of the pulses to vary the speed of the motor M in response to the degree of depression of the trigger T.

To the extent above disclosed, the FIG. 1 and 2 apparatus is conventional and is similar to the corresponding structure in the model No. 2102 surgical power drill marketed by the Assignee of the present invention.

Figure 4:
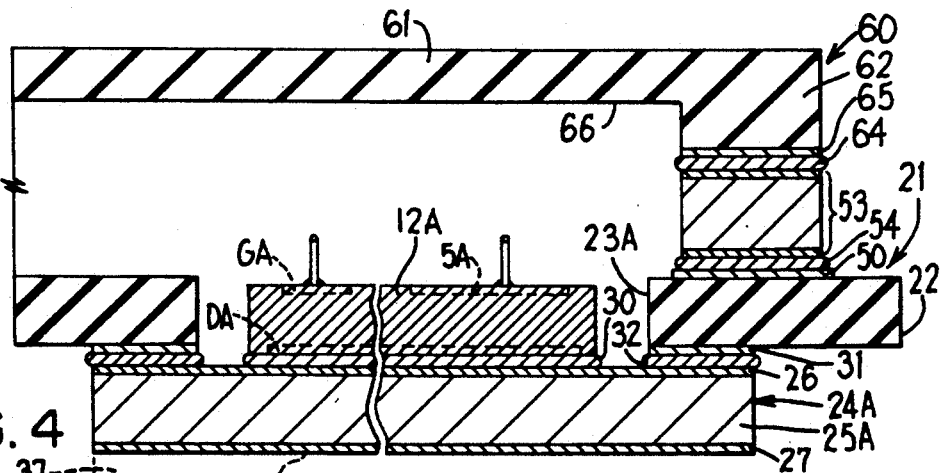
FIG. 4 is an enlarged fragmentary sectional view substantially taken on the line 4—4 of FIG. 3 and rotated 180° so as to appear in an upright position.

Turning now to structure more closely embodying the present invention, the FIG. 2 power semiconductors (here FET's) are physically arranged in a compact, hermetically sealed, heat dissipating motor control package 20, schematically indicated by the broken line rectangle in FIG. 2 and shown in structural detail in FIGS. 3 and 4.

Turning now to FIGS. 3 and 4, the package 20 comprises a P.C. board in the form of a composite plate 21. The composite plate 21 has a core 22 capable of withstanding relatively high operating temperatures, here a core 22 of conventional ceramic P.C. board material, of the kind available from Laserage Technology Corp. located at Waukegan, Ill.

The ceramic core 22 is a flat, plate-like member. Thin, electrically conductive foils hereafter discussed are fixed to the top and bottom surfaces of the core 22 in desired patterns, in a conventional manner, to complete the composite plate 21. In the embodiment shown, these are gold foils less than 0.001 inch thick fixed to the top and bottom surfaces of the ceramic core 22 by a conventional screening technique. This is conventional printed circuit board (P.C. board) construction and requires no further comment.

The FET's 12A–C are fixed with respect to the P.C. board 21 in the following manner. Holes 23A, 23B and 23C are provided through the P.C. board 21 in spaced relation to each other and to the perimeter of the board 21. The holes 23A–C exceed the length and width of the respective FET's 12A–C so that the respective FET's 12A–C fit loosely within the respective holes 23A–C without contacting the P.C. board 21.

Plural plate-like backers 24A, 24B and 24C close the bottoms of the respective holes 23A–C and electrically connect to a downward facing one of the main current electrodes, here the drain of each of the respective FET's 12A–C, as shown with respect to the drain DA shown in dotted lines of the FET 12A in FIG. 4.

The FET's 12A, 12B and 12C are all similarly installed with respect to the disclosed apparatus and the following description thereof with respect to the FET 12A will suffice for the FET's 12B and 12C as well.

In the particular embodiment shown, the backer 24A (FIG. 4) comprises a plate-like core 25A of electrically conductive material to which are fixedly and electrically conductively bonded thinner top and bottom layers 26 and 27 of electrically conductive material. The materials and thickness ratios of the backer 24A are selected to match the coefficient of thermal expansion of the P.C. board and particularly the relatively thick ceramic core 22 thereof. In the preferred embodiment shown, the backer core 25A is of molybdenum and the covering top and bottom layers 26 and 27 are of copper foil. The copper foils 26 and 27 can be secured to the molybdenum core 25A by metallurgical bonding.

In the embodiment shown, the drain DA of the FET 12A extends across the bottom thereof and is fixedly and electrically conductively connected to the top layer 26 of the backer 24A by a solder connection (here a solder layer) 30. The backer 24A overlaps the hole 23A lengthwise and widthwise and around the entire perimeter thereof and is fixed thereto in a manner to hermetically seal the bottom of the hole 23A. In the embodiment shown, the hermetic seal is provided as follows. A metal foil 31 is fixed to the bottom of the core 22 and extends entirely around the perimeter of the hole 23A. In the embodiment shown, the foil 31 is a gold foil fixed to the bottom of the ceramic plate by conventional screening techniques. A solder layer 32 is interposed between and fixedly bonds the foil 31 of the P.C. board 21 to the perimetral portion of the copper top layer 26 of the backer 24.

Figure 6:
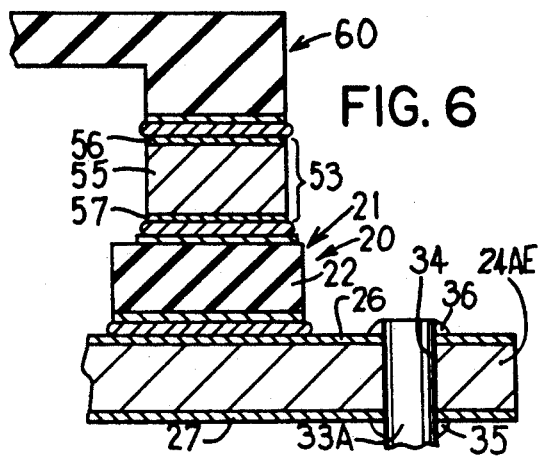
FIG. 6 is an enlarged fragmentary sectional view substantially taken on the line 6—6 of FIG. 3.

Each backer 24A–C, as seen in FIG. 3, extends beyond the adjacent edge of the P.C. board 21, as at 24AE in FIG. 6. A bore 34 extends upwardly through each backer extension, just outboard of the edge of the P.C. board 21. To make electrical connection to the drains DA–C of the FET's 12A–C for each FET, a respective wire (for example wire 33A of FIG. 4) of sufficient size as to carry the substantial drain current thereof is inserted upward into a bore 34 in the corresponding backer as at 24A in FIG. 6. For simplicity in manufacture, in the embodiment shown, the bore 34 penetrates through the layers 26 and 27 of the backer core 25. Each wire 33 is mechanically fixed to the respective backer 24A–C and placed in reliable electrical connection with the respective drain DA–C of the respective FET 12A–C by soldering to the outside of one or both of the conductive top and bottom layers 26 and 27 of the respective backer at 34. In addition, each backer 24A–C is of materials which make it an excellent heat conductor and is substantially larger and more massive than the respective FET 12A–C fixed on top thereof. Accordingly, each backer 24A–C also acts as an efficient heat sink to take away heat from its FET 12A–C generated by current passage through its FET and thereby to prevent excessive elevation of the temperature of its FET.

The bottom of each backer is relatively flat. Thus, if desired, a further heat sink mass, indicated in broken lines at 37 in FIG. 4, can be added by any convenient means in heat conducting relation to the corresponding backer. Slim conductor wires 42A, 42B and 42C (for example 0.001 inch diameter gold wires) make the FET gates GA, GB and GC respectively to conductive foils 43A, 43B and 43C fixed atop the P.C. board ceramic core 22 (FIG. 3) near the respective holes 23A–C.

The foils 43A–C connect through the mentioned resistors R1, R2 and R3 to respective elongate conductive foils 44A, 44B and 44C which lead in a direction away from the FET's 12A–C and have remote ends connected to the above mentioned conductive output lines 15A, 15B and 15C (FIGS. 2 and 3) of the control electrode actuator A. The foils 43A–C and 44A–C are fixed atop the ceramic core 22 of the P.C. board in a conventional manner, as by screening, as described above with respect to the metal foil 31. The foils 43A–C and 44A–C may be of gold. Thus, the respective conductors 15A–C from the control electrode actuator A of FIG. 2, all to supply control signals (here on-off signals) to the gates GA–C of the FET's 12A–C. In the embodiment shown, intermediate portions of the foils 44A–C are covered with glass insulating layers 45A–C respectively to maintain electrical isolation from a ground ring hereinafter described.

Figure 5:
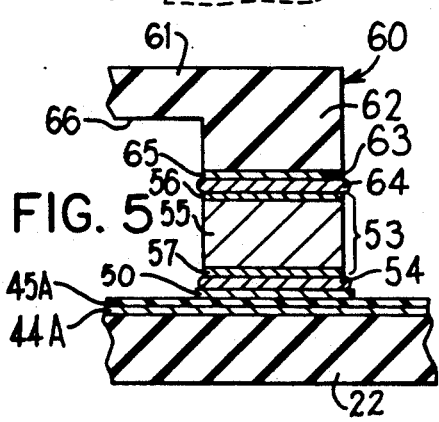
FIG. 5 is an enlarged fragmentary sectional view substantially taken on the line 5—5 of FIG. 3.

A further foil 50 of conductive material (here gold) is applied in the manner above described with respect to foil 31 but atop the plate-like ceramic core 22. The foil 50 defines a closed rectangular path loosely surrounding the FET's 12A–C, foils 43A–C, resistors R1–R3 and the inboard end portion of the foils 44A–C. The rectangular foil 50 overlies the glass insulative layers 45A–C. As seen in FIG. 5, the layers 50, 45A, 44A and 22 are continuously sealed each to the next and are thin enough that the top of the foil 50 is essentially flat despite crossing the extra layers at 44A–C and 45A–C.

Foils 51A, 51B and 51C (FIG. 3) are fixed on the upper surface of the P.C. board ceramic core 22 in the same manner as above described foils 43A–C and 44A–C but the foils 51A–C are located opposite the FET source electrodes SA–C respectively and are in fixed electric contact with the rectangular foil 50. Heavy current carrying wires 52A, 52B and 52C fixedly and electrically connect the FET source electrodes SA–C to the foils 51A–C respectively, here through respective 0.020 inch thick copper-molybdenum rectangular plates 101 (FIG. 8) soldered at 100 to the corresponding foils 51A–C and thus to the rectangular electrically conductive layer 50. Whereas the control signal carrying gate wires 42A–C are relatively slim (in one embodiment 0.001 diameter gold wires), the source wires 52A–C carry the full current passed by the FET's 12A–C and so are of substantially larger cross section (in one embodiment 0.015 inch diameter aluminum wires).

A ground ring 53 (FIGS. 3–6) is here rectangular in plan and corresponds in size and shape to the rectangular foil 50. The ground ring is fixedly and electrically secured atop the rectangular foil 50, hereby a solder layer 54 (FIG. 5), so as to loosely surround the holes 23A–C, the foils 43A–C, overlie the glass layers 45A–C and be in electrical contact with the source foils 51A–C. The ground ring 53 has a terminal tab 54 (FIG. 3) extending from one end thereof and beyond the P.C. board 21. The terminal tab 54 has fixedly and electrically connected thereto (as by soldering in the manner shown with respect to the wire 33 in FIG. 6) the common source conductor 13 above discussed with respect to FIG. 2.

The ground ring 53 is intended to match the thermal expansion characteristic of the composite plate (P.C. board) 21, while being electrically conductive through its thickness. In the preferred embodiment shown, the ground ring 53 is similar in composition to the backers 24A–C though of substantially less thickness. Thus, in one device constructed according to the invention, the ground ring had a total thickness of about 0.020 inch with about 80% of that thickness being a central core 55 (FIG. 5) of molybdenum, with flanking top and bottom layers each comprising about 10% of the thickness of the ground ring and being of copper.

A cover 60 is provided for the purpose of providing a hermetic seal over the top of the portion of the P.C. board surrounded by the ground ring 53. Thus, just as the backers 24A–C hermetically seal the bottom of the P.C. board 21, so to the cover 60 is to seal the top of the P.C. board. Accordingly, the FET's 12A–C, resistors R1–3, and their connections within the confines of the ground ring 53 are hermetically sealed against incursion of moisture by the backers 24A–C and cover 60.

In the preferred embodiment shown, the cover 60 is of bottom opening, otherwise closed, inverted rectangular box shape as seen in FIG. 7. The cover has a top 61 and depending side walls 62. The side walls 62 provide a continuous perimeter wall having a continuous bottom edge 63 sized and shaped to fit in face-to-face contact continuously around the ground ring 53. The cover 60 has substantially the same thermal expansion coefficient as the printed circuit board core 22. In the preferred embodiment shown, the cover 60 is constructed of the same ceramic material used for the core 22. The bottom edge 63 of the cover 60 is provided with a metallic foil 65 fixedly and continuously applied thereto in a conventional manner. The bottom edge foil 65 of the cover 60 is fixedly and continuously sealed atop the ground ring 53, preferably by a layer of solder 64. In this way, the cover 60 is rigidly fixed atop the ground ring 53 and is continuously hermetically sealed thereto around its entire periphery.

As a result, the backers 24A–C, P.C. board 21, ground ring 53 and cover 60 (with their various above-mentioned interposed fall, solder, etc.) layers define a hermetically sealed chamber 66 housing the FET's 12A–C to reliably protect same from moisture or other outside contamination, particularly as may be present in a surgical environment, while yet effecting the required control and high current connections to such FET's and while sinking excessive heat from the FET's to maintain same while below their maximum operating temperature despite high current flow therethrough.

As indicated above, the application of foils and insulative layers to the ceramic core 22 and cover 60 is carried out in a conventional manner. Soldering together of members is carried out conventionally, for example by stacking members with a solder layer interposed therebetween and then heating the stacked members in an oven to a temperature sufficient to melt the solder and create the solder joint.

Moreover, the thermal expansion coefficients of the core 22, backers 22A-C, ground ring 53 and cover 60 are matched, so that repeated expansion and contraction of the assembled package as a result of repeated heated and cooling cycles does not break the hermetic seals between the backers 24A-C, P.C. board 21, ground ring 53 and cover 60.

In one device constructed to the invention, peak currents of up to 50 amperes are passed by each FET. With operation at approximately 9 volts, power dissipation up to about 500 watts per FET has been encountered.

Although a particular preferred embodiment of the invention has been disclosed in detail for illustrative purposes, it will be recognized that variations or modifications of the disclosed apparatus, including the rearrangements of parts, lie with the scope of the present invention.

The embodiments of the invention in which an exclusive property or privilege is claimed are defined as follows:

1. A powered surgical handpiece, comprising:
   an electric battery;
   a drive motor energizable to drivingly move a tool;
   a control unit in circuit connection with said battery and motor for controlling energization of said motor, said control unit comprising:
   a P.C. board in the form of a composite plate having a ceramic core and electrically conductive cover layers fixed on opposite faces thereof and plural holes through said composite plate;
   plural semiconductor electric power control devices each having first and second electric current conducting electrodes, said electric power control devices fitting loosely in respective ones of said holes in said composite plate and out of contact with said composite plate, said electric power control devices tending to generate excess heat in operation;
   plural plate-like backers of heat and electric current conductive material, at least one of said backers having a first face fixedly bonded in heat and electric current conductive contact (1) with one face of said composite plate entirely around the perimeter of one said hole therein and effecting a hermetic seal of the corresponding end of said hole and (2) with the first electrode of one electric power control device loosely located in said hole, said one backer acting as an electric current path and at least part of a heat sink for said one electric power control device, said backers and said ceramic core having similar thermal expansion coefficients so as to maintain said hermetically seal;
   an electrically conductive ground ring electrically conductively fixed on the other face of said composite plate in electrically conductive relation therewith, said ground ring being electrically connected to the second electrode of said one device and acting a further electric current path;
   a cover of ceramic material with a thermal expansion coefficient similar to that of said core, said cover loosely overlying said devices and having a perimeter portion hermetically bonded entirely therearound with respect to said other face of said composite plate to form therewith and with said backers a hermetically sealed chamber containing said devices.

2. A compact, hermetically sealed, heat dissipating electric power unit, comprising:
   a P.C. board having a hole therethrough;
   a semiconductor electric power control device fitting loosely in the hole;
   a plate-like backer of heat and electric current conductive material bonded in heat and electric current conductive contact (1) with the P.C. board around the perimeter of the hole to hermetically seal the corresponding end of the hole and (2) with a first electrode of the device, the backer acting as an electric current path and at least part of a heat sink for the device, the backer and P.C. board having similar thermal expansion coefficients so as to maintain the hermetic seal;
   an electrically conductive ground ring electrically conductively fixed on the other face of the P.C. board and electrically connected to a second electrode of the device and acting as a further electric current path; and
   a cover of ceramic material having a thermal expansion coefficient similar to that of the P.C. board, said cover loosely overlying said device and having a perimeter portion sealed to the P.C. board to form therewith and with the backer a hermetically sealed chamber containing the device.

3. The power unit of claim 2 in which the ground ring fixedly bonds the perimeter portion of the cover entirely therearound with respect to the other face of said P.C. board to hermetically seal said chamber.

4. The power unit of claim 2 in which the P.C. board has a ceramic core, the conductive backer and the ceramic core and the cover being of materials selected to have substantially the same coefficient of thermal expansion, thereby avoiding breach of said hermetically sealed chamber despite increase in the temperature thereof during electric conduction by said device.

5. The power unit of claim 2 in which said backer comprises a molybdenum core sandwiched by substantially thinner copper faces.

6. The power unit of claim 2 in which said device is an FET, said first and second electrodes are the drain and source electrodes thereof respectively and said FET has at least one control electrode of relatively low current draw and including conventional conductive foil means extending from a connection to said control electrode and in insulating relation between said P.C. board and said ground ring to a terminal outside said sealed chamber.

7. The power unit of claim 2 in which said ground ring and said backer have terminal portions outside said sealed chamber for connection in an electric current loop including an electric power supply and a load.

8. The power unit of claim 7 in which the electric power supply and load are a battery and a drive motor.

9. The power unit of claim 8 in which the battery and drive motor are components of a portable surgical power tool.

UNITED STATES PATENT AND TRADEMARK OFFICE
CERTIFICATE OF CORRECTION

PATENT NO. : 5 136 469

DATED : August 4, 1992

INVENTOR(S) : Steven J. Carusillo et al.

It is certified that error appears in the above-identified patent and that said Letters Patent is hereby corrected as shown below:

Column 7, line 61; change "hermetically" to ---hermetic---.

Column 7, line 67; after "acting" insert ---as---.

Signed and Sealed this

Twenty-eighth Day of September, 1993

Attest:

BRUCE LEHMAN

Attesting Officer

Commissioner of Patents and Trademarks